United States Patent [19]

Omilinsky et al.

[11] 4,183,763

[45] Jan. 15, 1980

[54] GYPSUM-BASED GRANULES AND METHOD OF PRODUCTION

[75] Inventors: Barry A. Omilinsky, Morton Grove; Fredrick E. Wolatz, Brookfield, both of Ill.

[73] Assignee: Oil-Dri Corporation of America, Chicago, Ill.

[21] Appl. No.: 864,822

[22] Filed: Dec. 27, 1977

[51] Int. Cl.² ............................................. C04B 11/00
[52] U.S. Cl. ..................................... 106/109; 106/110
[58] Field of Search ................ 106/109, 110; 252/440; 423/555

[56] References Cited

U.S. PATENT DOCUMENTS 3,480,387  11/1969  Yasutake et al. ..................... 423/555
3,943,072  3/1976  Thomson et al. ..................... 252/440

*Primary Examiner*—James Poer
*Attorney, Agent, or Firm*—Dressler, Goldsmith, Clement, Gordon & Shore, Ltd.

[57] ABSTRACT

Calcium sulfate hemihydrate is processed into agglomerates such as granules and/or macrogranules by addition of an aqueous binder to a fluidized charge of calcium sulfate hemihydrate particles. The hemihydrate particles are agglomerated to a predetermined size range and hydrated to calcium sulfate dihydrate. The produced agglomerates have a bulk density of less than about 55 pounds per cubic foot, a surface hardness providing less than about 40 percent attrition, and a liquid holding capacity of at least about 10 percent.

5 Claims, 3 Drawing Figures

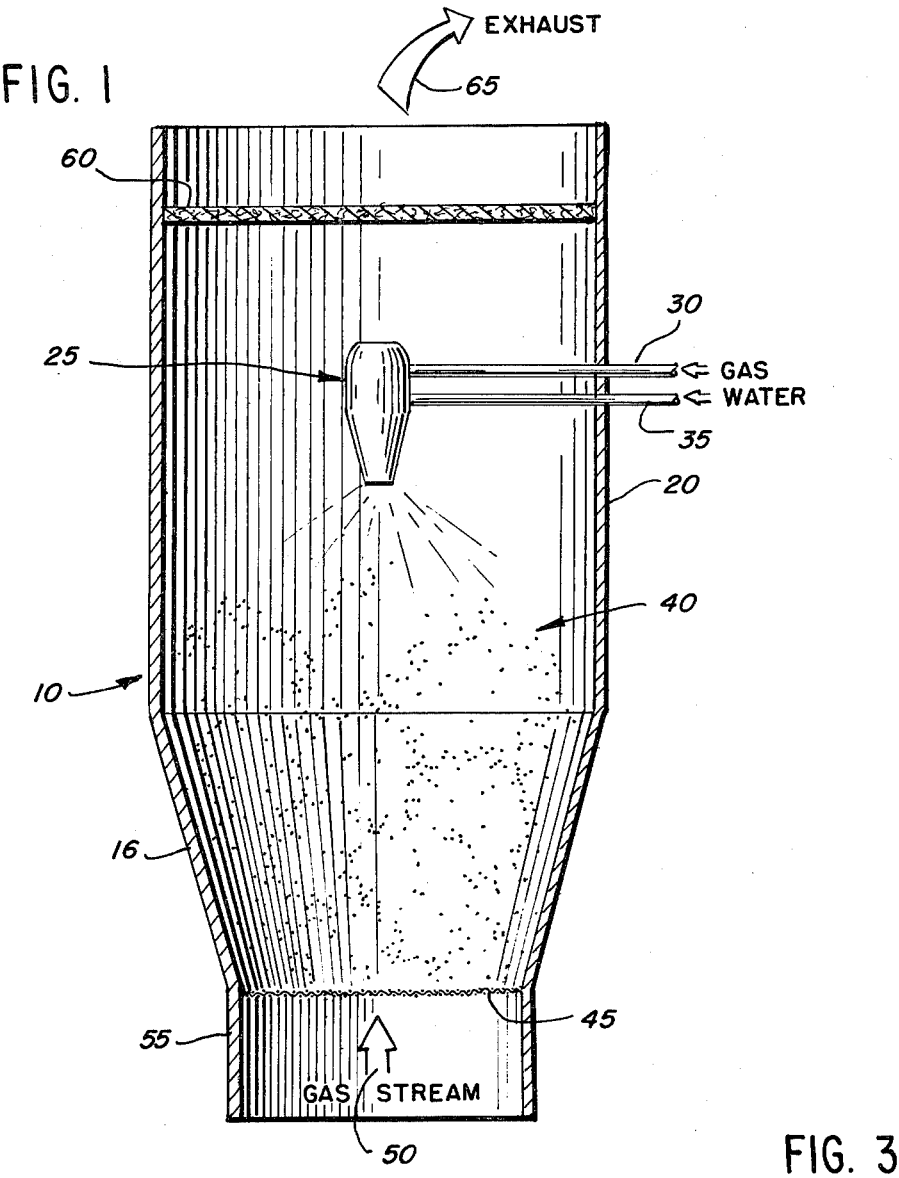
FIG. 1
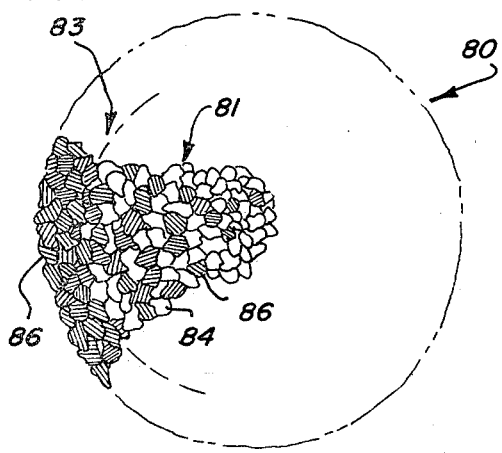
FIG. 2
FIG. 3

GYPSUM-BASED GRANULES AND METHOD OF PRODUCTION

BACKGROUND OF THE INVENTION

This invention relates to sorptive carriers and methods for producing granular sorptive carriers. In one aspect, the invention relates to a substantially neutral and inert carrier for agricultural chemicals which carrier comprises a granule of calcium sulfate dihydrate having certain beneficial properties.

A number of solid materials are widely used as carriers for agricultural chemicals, such as insecticides, herbicides, fertilizers, and the like. The agricultural chemicals are combined with such a carrier for convenient dissemination by various distributor means.

In some types of agricultural carriers, the chemical or active ingredient contained therein is in solid form, usually as a powder or as small particles or granules, and is admixed with the carrier, the mixture then being formed into pellets. With other types of carriers, the carrier is in the form of particles or granules into which the active ingredient, in liquid form, is absorbed. With yet another type of carrier the active ingredient is adhered to the carrier surface.

Agricultural carrier material can be used in many forms, such as powder, particles, granules, or pellets. For ease of handling, and for other reasons, materials having a granule size in a range which would pass through a 20-mesh screen and be retained on a 60-mesh screen (U.S.A. Standard Sieve Series) are commonly used. With such size granules, it is important that the granules maintain their structural integrity and thus size during initial fabrication as well as during subsequent storage, marketing, and application. In many applications, it is important that the particles or granules be of a size that does not pass through the 60-mesh screen so as to reduce the probability that some of the particles or granules are so small as to form dust. It is also important that the particles maintain their size and condition so that they do not form dust, or turn to dust, owing to degradation during storage or use, or owing to general abrasion or attrition during manufacturing, handling, storing, transporting and application with mechanical devices to agricultural soil. Dust is objectionable because of the well known problems with dust spreading in the air and on persons and animals, and being inhaled by workers making or handling such carriers.

Many naturally-occurring mineral carriers that are used with agriculturally active ingredients, including certain types of pesticides, have a degree of surface acidity which varies depending upon the crystalline and molecular structure of the mineral. It is thought that the surface acidity arises as a result of a non-uniform distribution of electric charge in or on the surface of the mineral particles. A large number of electric charges may exist at certain areas on a surface of a mineral carrier particle and these are referred to as acid sites or electrophilic centers. The strength of these centers varies depending upon the composition of the surface and the degree of distortion in the structure which brings about the non-uniform distribution of the electrical surface charges. The surface acidity on a mineral carrier particle can affect the reactivity of that mineral particle with the agricultural chemical carried thereon. It is thought that the surface acidity, and specifically the acid centers, have a catalytic effect with respect to the decomposition of the particular chemical. It has been found that with some pesticidal chemicals, the catalytic activity of the acid sites, with respect to inducing or accelerating decomposition, can be much reduced by deactivation of the acid sites with certain organic or inorganic materials which preferentially share their electrons with the mineral to form a bond which is stronger than that which may be formed between the agricultural chemical and the acid center itself. The addition of any deactivator material, usually in amounts of up to 6 to 8 percent by weight of the carrier adds an undesirable cost to the formulation of the agricultural chemical-laden carrier. Thus, it would be desirable to provide a substantially neutral and inert carrier for agricultural chemicals, and especially for pesticides, which has little or no surface acidity and which preferably does not require the use of any deactivator material in conjunction therewith to inhibit decomposition of the active ingredient (the carried chemical) on the carrier.

An absorbent carrier for liquid chemicals should have a relatively high sorptivity, or a sorptivity which is at least high enough to prove commercially satisfactory.

In the case of absorbent materials, the porosity of the material is usually related to the absorbency characteristics of the material. Further, a generally low dry bulk density is usually a characteristic of the more absorbent materials. Generally, as particle or granule size increases, the bulk surface area decreases for a given number of granules. Since sorptivity is principally a surface phenomena and a function of the pore density within a surface, it would be desirable to provide a carrier granule having a size small enough to present a relatively high bulk surface area and having a pore density high enough such that the sorptivity is commercially satisfactory. Further, the size of the particle cannot be so small as to constitute a powder or dust which is objectionable for the reasons previously explained or so small or friable that during manufacture large quantities of the carrier cannot be made without an undesirable amount of small, dust size particles being concurrently produced.

In order that a granulated carrier function properly and not degrade through abrasion or attrition into dust under mechanical stress during manufacture, packaging, storing, shipping and use, the carrier granules must exhibit adequate mechanical strength. Thus, it would be desirable to provide a carrier granule which has relatively high mechanical strength or resistance to attrition.

It would also be desirable to provide a carrier which is relatively inert and inexpensive, and one which can be made from relatively plentiful natural substance. One such substance is gypsum which occurs naturally in a form having the chemical formula $CaSO_4.2H_2O$. However, when naturally occurring gypsum is crushed into particles, the bulk density is about 65 to about 70 pounds per cubic foot. As discussed above, the higher the bulk density, the lower the sorptive capacity. Consequently, the sorptivity of such naturally occurring gypsum entities in the above-stated size range is relatively low, and in general is too low to provide a commercially acceptable sorptive carrier for agricultural chemicals in liquid form. However, the present invention provides relatively low-density gypsum granules that are eminently suitable as carriers for agricultural chemicals and a method for manufacturing these granules utilizing fluidized bed techniques under controlled conditions. Additionally, the low-density gypsum granules produced according to the present invention are useful as oil and grease absorbents, as absorbents for household pet toilets, and for similar applications.

SUMMARY OF THE INVENTION

According to the present invention, particles of calcium sulfate hemihydrate ($CaSO_4 \cdot \frac{1}{2}H_2O$) are agglomerated in a fluidized bed to produce a substantially inert, absorbent carrier suitable for use with agricultural chemicals. The present method is especially adapted for producing relatively high yields of discrete, porous calcium sulfate dihydrate ($CaSO_4 \cdot 2H_2O$)-containing granules of substantially uniform shape and having granule sizes within a predetermined range. The produced granules are relatively inert and have adequate sorptivity, good mechanical strength, good dry flow, and low dustability, and thus are very well suited for use as absorbents in general and as carriers for agricultural chemicals in particular.

According to the method of the present invention, a charge containing calcium sulfate hemihydrate particles is treated with an aqueous binder in a fluidized bed under controlled conditions. The charge is suspended in a fluidizing gas stream to form a fluidized bed or column, and a finely-divided aqueous binder in the form of atomized water, an aqueous solution, an aqueous suspension, fog, or the like, is discharged onto the fluidized bed thereby moistening the surfaces of the suspended particles and causing the formation of agglomerates such as granules or macrogranules of predetermined size while at the same time initiating the hydration of the calcium sulfate hemihydrate present which serves to bond the particles to one another. Thereafter the produced agglomerates are recovered and dried to remove excess moisture therefrom. Preferably, the agglomerates and any carried-over fines are screened so that granules of a desired size range can be separated from those that are undersized and oversized relative to the desired size. The oversized granules and/or macrogranules can be crushed to enhance the yield of granules within the desired size range while the undersized granules and carried-over fines can be reused in controlled quantities as part of the initial charge of particles to form, or complete the formation of, the desired size agglomerates in accordance with the basic method outlined above.

The granules formed in accordance with the method of the present invention preferably have a bulk density considerably lower than that of naturally-occurring gypsum, that is, less than about 55 pounds per cubic foot and preferably about 40 to about 55 pounds per cubic foot, as compared to 65 to about 70 pounds per cubic foot for naturally-occurring gypsum. Preferably, the granules of the present invention have a surface hardness providing less than about 40 percent attrition, and a liquid holding capacity of at least about 10 percent by weight. The method for measuring surface hardness and the liquid holding capacity are set forth in detail hereinbelow.

The granules manufactured in accordance with the method of the present invention are generally spheroidal in shape. In one preferred embodiment of this invention, the manufactured granules have a radially varying composition. That is, an interior core portion of the granule contains substantially more calcium sulfate hemihydrate than calcium sulfate dihydrate while an outer shell portion of the granule is substantially all calcium sulfate dihydrate. In another preferred embodiment of this invention, the produced granules are macrogranules which comprise discrete acervations or clusters constituted of a plurality of relatively smaller gypsum-containing granules that are surface-bonded to one another. The macrogranules have a bulk density that is at least about 5 percent less than the bulk density of said gypsum-containing granules that make up the macrogranules, and an average diameter at least about twice the average diameter of a majority of said gypsum-containing granules.

Numerous other advantages and features of the present invention will become readily apparent from the following detailed description of the invention, from the appended claims, and from the accompanying drawings.

BRIEF DESCRIPTION OF THE DRAWINGS

In the accompanying drawings forming part of the specification, and in which like numerals are employed to designate like parts throughout the same, FIG. 1 is a schematic diagram illustrating the method of producing the novel granules in accordance with the present invention;

FIG. 2 is an enlarged schematic representation of the cross-section of one embodiment of the granule produced in accordance with the method of the present invention; and FIG. 3 is an enlarged perspective view of a macrogranule embodying the present invention.

DESCRIPTION OF THE PREFERRED EMBODIMENTS

While the method and product of this invention are susceptible of embodiment in many different forms, there are shown in the drawings and will herein be described in detail specific embodiments, with the understanding that the present disclosure is to be considered as an exemplification of the principles of the invention and is not intended to limit the invention to the embodiments illustrated.

All references made herein to sieve analyses, screen mesh sizes, particle sizes, and the like are based on U.S.A. Standard Sieve Series—ASTM Specification E-11-70.

In accordance with the present invention, an agglomerate is produced which comprises (1) macrogranules and/or granules of calcium sulfate dihydrate or (2) macrogranules and/or granules of a combination of calcium sulfate hemihydrate and calcium sulfate dihydrate. Particulate absorbent fillers such as gypsum fines, clay fines, and the like, can also be present.

The granules of this invention have a dry bulk density of less than about 55 pounds per cubic foot, preferably about 40 to about 55 pounds per cubic foot. These granules have a surface hardness of less than about 40 percent attrition and a liquid holding capacity of at least about 10 percent by weight. The present invention also contemplates macrogranules that comprise a plurality of one or both of the foregoing types of granules surface-bonded to one another. The macrogranules have a substantial internal void space and thus a bulk density less than that of the individual granules. While the surface hardness of the macrogranules is quite good and sometimes exceeds that of the individual granules that constitute the macrogranule, the macrogranules can be reduced in size by crushing so as to produce an enhanced yield of granules within a predetermined size range.

The structure, liquid holding capacity characteristics, and the dry bulk density characteristics of the granule of this invention provide the granule as well as the macrogranule constituted from a plurality of such granules with an absorption capacity and other physical properties which render it useful as a carrier for chemicals in liquid form or as an absorbent for various other liquids.

The fact that the surface hardness of the granules of this invention is less than about 40 percent attrition is an indication that the granule of the present invention is particularly well suited for commercial use as a carrier for liquid chemicals, and especially as a carrier for agricultural liquid chemicals, which are sorbed in or on the granule and which can be deposited upon agricultural sites by spreading the granules on such sites using ordinary agricultural implements. Specifically, the relatively high surface hardness imparts a degree of mechanical strength or resistance to attrition under the mechanical stresses encountered during the formulation process, during packaging, and shipping, as well as during use when the granules are spread by mechanical apparatus on agricultural sites.

The relatively high surface hardness further contributes to a relatively low dustability characteristic of the granule. That is, the granule of the present invention, having a relatively high surface hardness, has a lesser tendency to break down and form small dust particles or "fines" which are generally undesirable because the fines spread through the air and are transported to areas where they are not wanted and also because they may be inhaled by animals and/or workers handling the granules.

The calcium sulfate dihydrate agglomerates as well as the hemihydrate/dihydrate agglomerates of the present invention provide granules which are substantially inert with respect to the agricultural chemicals for which they are intended to serve as a carrier. It is believed that this carrier material has few, if any, catalytic sites or acid sites, which tend to cause or accelerate decomposition of various chemicals absorbed on the granules. Thus, the use of deactivator compounds is not ordinarily required with this granule to neutralize acid centers as is required with many other types of carriers. It is believed that deactivators used with naturally occurring mineral clay carriers account for ¼ to ⅓ the price of the average clay mineral carrier. Therefore, the use of the granules of the present invention could provide substantial savings resulting from the elimination of some or all of the amount of deactivators which must be currently used with the naturally occurring mineral clay carriers.

It is to be noted that the calcium sulfate dihydrate granule of the present invention has a bulk density of less than about 55 pounds per cubic foot when prepared in accordance with the method of the present invention to be described hereinafter. This compares favorably with the bulk density of naturally occurring gypsum (calcium sulfate dihydrate) of between 65 and 70 pounds per cubic foot. Though this reduction in bulk density cannot be currently satisfactorily explained, such a reduction in bulk density is highly desirable because it is some indication of the sorptivity capability, i.e., liquid holding capacity, of the granules. The liquid holding capacity of the granules of the present invention is at least about 10 percent by weight, and usually is about 12 percent by weight and higher. In contradistinction thereto, the liquid holding capacity of naturally occurring gypsum usually is of the order of about 3 to 4 percent by weight.

The preferred size of the granule of the present invention falls within a range wherein the granule will pass through a 20-mesh screen and be retained on a 60-mesh screen. This size granule has dry flow characteristics and handling characteristics that make it eminently suitable for use as a carrier of agricultural chemicals.

The granule of the present invention is produced in accordance with a method which forms part of the present invention. This method is schematically illustrated in FIG. 1 and reference is directed thereto. In accordance with the method of the present invention, the granules are produced in a fluidized bed apparatus, such as a granulator schematically illustrated as 10 in FIG. 1. Typical fluidized bed apparatus suitable for use with the method of the present invention are the Glatt granulators, Models WSG-5, -15, -30, and -60 produced by Werner Glatt, Spezialschnelltrockner-Lufttechnischer Apparatebau, D-7851 Binzen-Kr., Lörrach, West Germany.

The fluidized bed apparatus 10 is a generally vertically upstanding column comprising a generally conical shaped product container 16, a generally cylindrical spray housing 20, and a spray nozzle 25 disposed within the spray housing 20 above the product container 16. A pressurized atomization gas, such as air or the like, may be fed to the nozzle through conduit 30 and an aqueous binder, such as liquid water, may be fed through the spray nozzle 25 and conduit 35.

The charge 40 of particles to be fluidized, such as particulate calcium sulfate hemihydrate with or without fines, other additives, or inert substances or fillers, is retained within the product container 16 on a screen or perforated plate 45. The charge 40 of particles to be agglomerated or granulated is maintained in a fluidized state during processing by a gas stream such as air designated by arrow 50 entering the bottom of the product container 16 through a duct 55 and passing from the duct 55 through the screen 45 into and through the charge 40. The gas stream is passed through the charge at a velocity sufficient to expand the bulk volume of charge 40 and to set in motion the particles constituting charge 40. The fluidizing gas stream is adjusted to maintain the particles in suspension above the screen 45 without carrying any significant amount of the particles out of the fluidized bed region. The quality of fluidization is not overly critical, i.e., the fluidization can be of the smooth, bubbling, or slugging type, as desired.

A filter apparatus 60 is disposed at the top of the spray housing 20 to trap any small particulate matter that may have been entrained with the gas stream and carried out of the fluidized bed region. The gas stream exhausts as indicated by arrow 65 at the top of the fluidized bed apparatus 10. The exhaust gas stream is typically recirculated and introduced to the inlet of a blower (not illustrated) which circulates the fluidizing gas.

It is also possible, through common devices not illustrated, to add moisture to the incoming gas stream and to heat or cool the incoming gas stream as dictated by the process requirements. The flow of the incoming gas stream can also be regulated by inlet and outlet dampers (not illustrated) as desired. The fluids introduced through the nozzle 25 via conduits 30 and 35 are also typically controlled with respect to flow rate and/or pressure by conventional process apparatus not illustrated here but familiar to those skilled in the art. Additionally, the height of the nozzle 25 above the bed plate 45 may be adjusted as required.

With the particles of charge 40 suspended in the gas stream in the product container 16, an aqueous agglomerating or binder means such as liquid water or aqueous solutions or suspensions is introduced through the nozzle 25 whereby the individual particles of charge 40 become wet or coated with the introduced binder means. When the small particles are suspended in fluidized bed 10 and sprayed with an aqueous binder from the nozzle 25 for a predetermined time period, it has been found that the small particles impinge upon one another and coalesce to agglomerate into larger particles such as granules or even acervations or clusters of granules.

In practicing the method of the present invention a fluidizable charge containing particulate calcium sulfate hemihydrate is charged to product container 16 of the granulator, is fluidized by a gas stream and then agglomerated as hydration of the calcium sulfate hemihydrate present is initiated by the introduction of a binder liquid. Usually the fluidizing gas stream is at a relative humidity of somewhat less than 100 percent, preferably at a relative humidity of about 85 to about 95 percent in order to minimize excessive losses of water from the binder to the fluidizing gas stream.

The fluidizable charge can be all calcium sulfate hemihydrate, or the charge can be constituted by the hemihydrate in combination with calcium sulfate dihydrate fines derived from earlier granulation runs, absorbent clay fines, or the like, with or without other finely-divided particulate materials, such as inert substances, fillers, or the like, being present. In any event, the fluidizable charge should contain at least about 35 percent by weight, and preferably at least about 50 percent by weight of calcium sulfate hemihydrate.

The presence of fines in the charge affects the surface hardness of the ultimately produced absorbent granule, thus the surface hardness can be regulated by controlling the amount of fines present in the fluidizable charge. In general, the fluidizable charge can contain up to about 50 percent by weight fines. The higher the concentration of these fines in the fluidizable charge the lower will be the surface hardness of the ultimately produced granules.

At a given concentration level of fines in the fluidizable charge, the moisture content of the fines is also an important factor in determining the surface hardness of the produced granules. This is so because the fines are good absorbents albeit of relatively small particle size, usually passing through a 60-mesh screen and preferably passing through a 325-mesh screen, and compete with the hemihydrate particles in the fluidizable charge for the moisture that is introduced into the fluidized bed as the binder. Accordingly, it has been found that for optimum results it is preferable to pre-wet or load the fines with water before hydration of the calcium sulfate hemihydrate present is initiated. Pre-wetting of the fines can be achieved by initially fluidizing a charge of fines and wetting the fines by treatment with a water spray before any of the calcium sulfate hemihydrate particles are introduced into the fluidized charge. In the alternative, a separate supply of pre-wet fines can be prepared which are then comingled with the hemihydrate particles to be granulated, and the resulting admixture is then fed to the granulator and is fluidized. The fines can be pre-wet with water up to the maximum liquid holding capacity for the particular fines that are being used, that is, after pre-wetting the fines still should retain the properties of a free-flowing powder and should be readily fluidizable.

The incorporation of calcium sulfate dihydrate fines into the fluidizable charge, and in particular the incorporation of wet calcium sulfate dihydrate fines, also decreases the granulation time as well as the set time, i.e., the rate of hemihydrate conversion to the dihydrate is accelerated. Furthermore, the incorporation of the dihydrate fines narrows the size distribution range of the produced granules and, in general, tends to produce granules of a smaller average diameter.

To fluidize the charge, a convenient fluidizing gas is air in view of its ready availability and low cost. However, for certain applications, e.g., where a readily oxidizable agricultural chemical is granulated together with the hemihydrate particles, the fluidizing gas can be an inert gas such as carbon dioxide, nitrogen, helium, argon, and the like. The fluidizing gas can be at ambient temperature, but preferably is pre-heated to a temperature of about 115° F. (45° C.) to about 150° F. (65° C.) in order to modify the rate of hemihydrate hydration or setting.

The humidity of the fluidizing gas can be controlled as required by the granulation process conditions, as pointed out hereinabove. Also, in some instances it is desirable to effect partial drying of the formed granules while they are still within the granulator. In such cases the rate and degree of drying can be controlled by adjusting relative humidity of the incoming gas stream so that the gas stream leaving the fluidized bed and exiting from the granulator will be substantially saturated with respect to water vapor. Drying of the produced granules is also facilitated by the hydration itself inasmuch as the exotherm of hydration from the hemihydrate to the dihydrate elevates the temperature of the individual granules and/or macrogranules present and drives off some of the water that has been initially deposited on the individual particles that constitute the initial charge to the fluidized bed.

In order to properly fluidize the charge containing calcium sulfate hemihydrate, the particles constituting the fluidizable charge should have a reasonably uniform size and density. It is also necessary that the charge introduced into the granulator disperses into more or less discrete particles as the fluidizing gas is passed therethrough. For the purposes of the present method the particle size of the fluidizable charge preferably is such that no more than about three percent of the dry charge is retained on a 50-mesh screen and that substantially no particles greater than about one-third of the diameter of the desired granule diameter are present in the charge. Preferably at least about 50 percent, and more preferably at least about 75 percent, of the charge passes through a 325-mesh screen. The fluidizing gas velocity should be such as to fluidize most of the larger particles that are present.

Hydration of the hemihydrate can be accomplished by introducing into the fluidized charge a predetermined amount of the aqueous binder in the form of a water spray, fog, steam, a spray of an aqueous solution containing additional binders or setting accelerators, a spray of an aqueous suspension of dihydrate fines, and the like. A convenient means for the introduction of any kind of a spray is a nozzle such as spray nozzle 25.

While the nozzle design is dependent to some extent on the nature and viscosity of the agglomerating or binder means that is to be dispersed over the fluidized bed, a wide variety of nozzle designs will give satisfactory performance. In some cases a gas under pressure can be utilized to deliver the aqueous binder through the nozzle, and the pressure thereof, together with the nozzle orifice size, determines the size of the liquid droplets that are generated. In other cases a spray nozzle having a predetermined orifice size can be used. In any event, the amount and size of the introduced finely-divided binder entities determine the extent and kind of agglomeration (e.g., granules or macrogranules) and thus the particle size of the agglomerated product. If the binder droplets are too large, oversize agglomerates will be produced, but if the droplets of the binder are too finely atomized, very little agglomeration will be effected. With water or aqueous liquids or suspensions of similar viscosity a droplet size of the order of about 1 micron or less to about 1000 microns is preferred; more preferred is a droplet size of about 1 to about 500 microns.

For the purposes of the present invention it is preferable that the amount of water added to the fluidized charge is in excess of the amount stoichiometrically necessary to effect complete hydration of the calcium sulfate hemihydrate that is present. More preferably, water is supplied to the fluidized charge in an amount that exceeds the stoichiometric amount needed to convert the hemihydrate to the dihydrate by about 15 to about 50 percent by weight. A larger excess of water is undesirable because the fluidized bed tends to collapse, and the granulation efficiency tends to suffer. Additionally, more energy has to be expended during subsequent drying of the produced granules if too much water is present. In order to produce granules containing some hemihydrate as well, the amount of water added to the fluidized charge usually is less than the amount necessary for complete hydration of the hemihydrate initially present in the charge.

The rate of water addition to the fluidized charge can vary depending on the desired size of the granules and/or macrogranules that are to be produced. Usually water is introduced into the fluidized charge at a substantially constant rate until such time when the fluidized charge contains about 10 percent by weight or less discrete hemihydrate particles.

To produce calcium sulfate dihydrate agglomerates that are granules predominantly in the size range of about 20/60 mesh, water is sprayed onto a fluidized charge of about 50 pounds in the granulator in relatively small droplets over a time period of about 5 to about 15 minutes, after which time period granulation is complete and the produced granules are withdrawn from the granulator for further drying. On the other hand, to produce calcium sulfate dihydrate agglomerates that are macrogranules predominantly in a size that is retained on a 20-mesh screen, substantially the same amount of water is sprayed onto the same fluidized charge in relatively large droplets and for a time period of about 3 to about 5 minutes.

Hydration of the calcium sulfate hemihydrate present in the fluidized charge bonds the agglomerated particles together. Hydration is initiated during the granulation processes that take place within the fluidized bed but need not be completed by the time the granulation processes are completed and the charge is withdrawn from the granulator. That is, the produced granules and/or macrogranules can be hardened or set by extending their residence time in the granulator or during a subsequent drying step after recovery from the granulator in a surface-wet condition. The rate of hydration can be controlled by the addition of additives that speed up or retard hydration as desired. For example, without additives, the hydration time of the produced agglomerates is about 30 minutes, but with additives the hydration time can be adjusted from about two minutes to about 24 hours. The granulation of a charge of about 50 pounds within the fluidized bed is usually completed within a time period of about 2 to about 20 minutes, depending on the initial particle size in the fluidized charge, the quality of fluidization, the presence of fines, the rate of water introduction, the desired agglomerate size, and similar factors. The hydration may or may not be complete when the produced agglomerates leave the fluidized bed; however, the produced agglomerates should exit from the granulator as coherent, discrete entitles within a predetermined size range.

At this stage, the produced agglomerates are still wet with excess water (usually about 5 to about 15 percent by weight free moisture) which aids in preserving agglomerate integrity during handling, i.e., during granule and macrogranule recovery from the granulator. After hydration is completed, however, the bonded agglomerates are dried in an air stream or in any other convenient manner, usually at a temperature of about 100° F. to about 120° F., and classified. Inasmuch as the hydration of calcium sulfate is a reversible process, drying temperatures in excess of about 150° F. should be avoided.

As pointed out hereinabove, by effecting certain variations in the method of the present invention so as to provide a limited amount of water for hydration, granules can be made which comprise both calcium sulfate hemihydrate and calcium sulfate dihydrate. Specifically, with reference to FIG. 2, such a granule 80 is illustrated as having a substantially spheroidal form. In granule 80, an inner core portion 81 comprises predominantly hemihydrate particles 84 and is substantially surrounded by an outer shell portion 83 consisting essentially of calcium sulfate dihydrate particles 86. The outer shell portion 83 is relatively harder than the inner core portion 81. Compared to the outer shell portion 83, the inner core portion 81 is relatively more friable and usually contains more calcium sulfate hemihydrate than calcium sulfate dihydrate, whereas the outer shell portion 83 is substantially all calcium sulfate dihydrate. The composition of the granule varies radially outwardly from the center of the inner core portion with the proportion, or concentration of, calcium sulfate dihydrate increasing with increasing radial distance from the center of the inner core portion.

A macrogranule embodying the present invention comprises an agglomerate constituted of a plurality of individual gypsum-containing, i.e., calcium sulfate dihydrate-containing, granules and is illustrated in FIG. 3. Macrogranule 88 is made up of relatively smaller individual granules, such as granules 90, 92 and 94 contiguous with and surface-bonded to one another. Macrogranules, such as macrogranule 88, have a substantial internal void space and, as a result a bulk density that is less than the bulk density of the individual gypsum granules that make up the macrogranules. Preferably, the bulk density of the macrogranules is at least about 5 percent less than the bulk density of the individual granules. Each macrogranule comprises three or more granules surface-bonded to one another so as to provide at least one internal void space and have an effective diameter that is at least about twice the effective diameter of the majority of the individual granules.

While the individual particle size of the gypsum granules that make up the macrogranules varies, surprisingly it has been found that the particle size distribution of these granules falls within a relatively narrow range. For example, when gypsum macrogranules retained on a 20-mesh screen are crushed to generate the discrete, low-density gypsum granules that initially made up the macrogranules, a major portion of the generated granules pass through the 20-mesh screen and are retained on a 60-mesh screen. In some instances substantially no granules passing through the 60-mesh screen have been produced.

The foregoing characteristics can be advantageously utilized for the manufacture of absorbents and/or carriers for agricultural chemicals having a relatively closely controlled particle size. That is, the granulation process parameters can be selected so as to maximize the production of 20/60 mesh gypsum granules by producing agglomerates that are primarily macrogranules of a size retained on a 20-mesh screen and which macrogranules can be subsequently crushed to produce substantial yields of 20/60 mesh gypsum granules. To this end, particle agglomeration is carried out by introducing into the fluidized bed the aqueous binder liquid, preferably water, over a relatively short time period, e.g., about 3 to 5 minutes, so as to produce agglomerates at least about 15 percent by weight of which are of a size retained on a 20-mesh screen. After the produced agglomerates are dried, the +20 mesh agglomerates are segregated and crushed into granules passing through 20-mesh screen but retained on 60-mesh screen.

A number of examples will be presented hereinafter for the purposes of further illustrating and disclosing the present invention. These examples are by way of illustration, and are not to be taken as limiting.

With each example, there is provided a tabulation of parameters relating to the initial charge of material, the process conditions, and the characteristics of the final product. Certain terms or properties that have been used or referred to in the present specification, including the following examples, are defined or determined as follows:

(1) "Bulk Density" is the measured loose packed density of the agglomerated product when dried to no more than 1 wt.-% free moisture. A 250 ml. graduated cylinder is completely filled with the product without tamping. The bulk density in pounds per cubic foot is determined by dividing the weight of the sample in grams by the volume of the sample in milliliters and multiplying by the factor 62.43.

(2) "Water Absorption" is determined by the following procedure. First, a sample of about 50 grams from the dried product is weighed to the nearest 0.1 gm. and poured into a glass tube measuring 9 inches in length and 30 mm. in internal diameter. The glass tube is maintained in a vertical position and one end of the tube is covered with a Number 18-mesh screen. Fine particles passing through the screen are collected and returned to the top of the tube. The glass tube is held on a tripod stand and positioned at a 30° angle to the horizontal. A 100 ml. graduated cylinder is placed under the tube at the screen.

75 ml. of water is introduced from a pipette through the open end of the 9-inch-long glass tube to the sample. The water is absorbed by the sample until the saturation point is reached and the surplus water begins draining into the graduated glass cylinder. This step is continued until all portions of the sample in the tube are wet. After insuring that no part of the sample in the tube is dry, the tube is allowed to drain for 30 minutes. Next, since 75 ml. of water was initially present in the pipette, and since any water not absorbed by the sample in the tube is collected in the graduated cylinder below the tube, the amount of water absorbed is equal to the initial 75 milliliter quantity minus the volume of water collected in the graduated cylinder. This amount is divided by the weight of the sample in grams to provide the absorption capacity of the sample in units of ml./gm.

(3) "Oil Absorption" was determined in accordance with the test specified in Bulletin P-A-1056, Federal Specification, Absorbent Material, Oil and Water (For Floors and Decks), issued by the General Sevices Administration of the United States of America. The observed absorption capacity is reported in units of ml./gm.

(4) "Surface Hardness" is reported as percent attrition and is determined as follows: A nest of two standard testing sieves, sieve No. 8 and sieve No. 60, each having a circular shape and an eight-inch diameter, are selected for use with a Ro-Tap mechanical sieve machine manufactured by W. S. Tyler Co. of Dayton, Ohio. An aliquot of 100 grams, weighed to the nearest 0.1 gm., is withdrawn as a sample from the granulated product. The sample is placed on the No. 8 sieve in the sieving machine for 5 minutes of shaking. The material passing through both the No. 8 sieve and the No. 60 sieve and ending up in a collecting pan beneath the No. 60 sieve is rejected along with any larger material unable to pass through the No. 8 sieve. 50 grams of material retained on the No. 60 sieve is placed in a pan along with 300 grams of ¼-inch diameter steel balls and hand mixed. The pan is then shaken in the mechanical sieving machine for 20 minutes without the tapping arm engaged. The contents of the pan are placed on the top, No. 8, sieve and allowed to fall through to the No. 60 sieve and retaining pan below the No. 60 sieve. The steel balls are removed from the No. 8 sieve and the machine is mechanically sieved for 5 minutes with the tapping arm engaged. The material that is passed through the No. 60 sieve is then weighed. The hardness, in terms of "break down percent" or attrition is calculated by dividing the weight of the material that has passed through the No. 60 sieve by 50 grams and multiplying by 100.

(5) "Liquid Holding Capacity". In testing liquid holding capacity (dry flow), a low viscosity organic liquid having a specific gravity of 1 gm./ml. is used. A one to one mixture (by weight) of Heavy Aromatic Naphtha and ortho chloro toluene will give the desired specific gravity and viscosity, and be relatively non-volatile. The procedure is as follows:

(A) Place 20 grams of granules in an 8-ounce French square bottle.

(B) Add 5-gram increments of liquid to the granules and for each increment shake the bottle (a) until no granules cling to the sides or (b) for 5 minutes.

(C) When sufficient liquid has been added that granules still cling to the sides of the glass after 5 minutes of shaking, add 1-gram increments of dry granules (with a 5 minute shaking interval for each addition until the point is reached where no granules cling to the sides of the container). At this point the liquid holding capacity (L.H.C.) is calculated as follows:

$$\% \, L.H.C. = \frac{\text{cc (or grams) of liquid}}{\text{grams of granules + grams of liquid}} \times 100$$

(6) The "Screening Distribution Analysis" presented in each example summarizes the results of a standard test to determine the distribution of granule sizes in the product charge. At the end of the granulation process, the batch of produced granules was dried. Thereafter, five standard circular, 8-inch diameter sieves or mesh screens were used in the analysis and were placed in nested, descending order with respect to screen size (mesh opening). Approximately 200 grams of the granule product was placed on the top sieve, and the sieves were shaken for five minutes using a Ro-Tap mechanical sieve machine. The weight retained on each tared sieve was converted to percent retention of the 200-gram sample and is listed in the tabulation for each example under the sieve or mesh number on which it is retained. A listing of a a pair of sieve or mesh numbers separated by a virgule (/) indicates that the granules had passed through the first number sieve or screen and had been retained on the second number sieve or screen. A sieve or mesh number preceded by a plus (+) sign indicates that the granules were retained on the sieve or screen, whereas a sieve or mesh number preceded by a minus (−) sign indicates that the granules passed through the sieve or screen.

EXAMPLE 1

Model WSG-15 Glatt fluidized bed granulator was used to treat charges of commercial grade gypsum plaster.[1] In each instance the charge was fluidized using ambient air heated to a temperature of about 115° F. (about 45° C.). The binder in each instance was water, sprayed at a predetermined rate through a Schlick spray nozzle having an interchangeable orifice. Water add-on for each run was determined using Speedy Moisture Tester Type D.1 manufactured by Thomas Ashworth & Co., Ltd. and commercially available from Soil Test Laboratories, Northfield, Illinois. The processing parameters for each charge and the obtained experimental results are tabulated hereinbelow in Table I.

[1] industrial plaster—O.D., obtained from U.S. Gypsum Company, having 82% min. rehydrated purity and a particle size distribution such that no more than 3% is retained on a 50-mesh screen and at least 90% pass through a 100-mesh screen.

TABLE I

| Run | Charge Size, lbs. | Run Time, min. : sec. | Atomization Press., bars | Nozzle Orifice, mm. | Water Sprayed, ml. | Water Add-On, wt. % | Approximate Size Distribution, mesh |||
|---|---|---|---|---|---|---|---|---|---|
| | | | | | | | % +20 | % 20/60 | % −60 |
| A | 30 | 2:15 | 2 | 1.8 | 2880 | 20 | 43.2 | 33.0 | 24.0 |
| B | 30 | 4:00 | 2 | 1.2 | 3320 | 18 | 41.2 | 38.2 | 20.6 |
| C | 30 | 4:45 | 3 | 1.2 | 3450 | 20 | 47.0 | 36.0 | 16.0 |
| D | 30 | 5:00 | 3 | 1.2 | 3500 | 22 | 49.6 | 31.4 | 19.0 |
| E | 40 | 2:50 | 2 | 1.8 | 3570 | 19 | 41.0 | 32.0 | 26.5 |
| F | 40 | 3:00 | 5 | 1.8 | 3700 | 18 | 50.8 | 24.9 | 24.3 |
| G | 45 | 3:30 | 2 | 1.8 | 4320 | 21 | 52.8 | 30.2 | 17.1 |
| H | 45 | 3:40 | 2 | 1.8 | 5200 | 21 | 60.1 | 23.6 | 15.6 |
| I | 55 | 4:00 | 2 | 1.8 | 5000 | 20 | 54.4 | 25.0 | 20.4 |
| J | 60 | 4:00 | 2 | 1.8 | 4750 | 18 | 47.0 | 25.3 | 27.6 |
| K | 60 | 4:00 | 5 | 1.8 | 5250 | 18 | 46.4 | 27.1 | 27.1 |
| L | 50 | 3:30 | 2 | 1.8 | 4300 | 19 | 43.2 | 31.1 | 25.7 |
| M | 50 | 9:00 | 2 | 1.2 | 5250 | 18 | 70.7 | 21.0 | 8.3 |
| N | 50 | 9:00 | 3 | 1.2 | 4500 | 15 | 18.4 | 34.2 | 47.2 |
| O | 50 | 9:00 | 3 | 1.2 | 5370 | 18 | 24.3 | 37.6 | 39.3 |
| P | 50 | 9:00 | 3 | 1.2 | 6000 | 20 | 35.2 | 34.1 | 30.7 |
| Q | 50 | 9:00 | 3 | 1.2 | 6700 | 21 | 41.6 | 34.5 | 23.8 |
| R | 50 | 9:00 | 3 | 1.2 | 7120 | 23 | 55.7 | 30.0 | 14.4 |
| S | 50 | 10:00 | 3 | 1.2 | 5800 | 19 | 16.9 | 33.5 | 49.5 |
| T | 50 | 9:00 | 4 | 1.2 | 5350 | 18.5 | 17.6 | 33.5 | 48.9 |
| U | 50 | 8:10 | 5 | 1.2 | 7200 | 19 | 38.3 | 31.7 | 30.0 |
| V | 50 | 8:30 | 5 | 1.2 | 7200 | 21 | 32.7 | 36.7 | 30.4 |
| W | 50 | 8:30 | 5 | 1.2 | 7200 | 23 | 43.4 | 33.5 | 23.1 |
| X | 50 | 9:00 | 5 | 1.2 | 6800 | 21 | 55.6 | 26.5 | 17.9 |
| Y | 50 | 9:00 | 5 | 1.2 | 6100 | 19 | 23.3 | 34.3 | 42.4 |
| Z | 50 | 9:00 | 5 | 1.2 | 6800 | 21 | 27.0 | 39.6 | 33.4 |
| AA | 50 | 9:00 | 5 | 1.2 | 7450 | 23 | 34.1 | 39.8 | 26.2 |
| AB | 50 | 9:00 | 5 | 1.2 | 5400 | 16 | 17.7 | 28.2 | 54.1 |
| AC | 50 | 9:00 | 5 | 1.2 | 6800 | 21 | 19.5 | 31.2 | 49.3 |

EXAMPLE 2

In the same granulator as used in Example 1, fluidized charges of about 50 pounds and comprising the same gypsum plaster as used in Example 1 together with varying amounts of fines pre-wet with water were fluidized with air at about 115° F. (45° C.) and granulated using water as the binder. The processing conditions were as follows:

| | |
|---|---|
| Atomization Pressure, bars | 3 |
| Nozzle Orifice, millimeters | 1.8 |
| Total Water Add-On,[2] wt. % | |
| $CaSO_4 \cdot 2H_2O$ | |
| −60 mesh | 20–21 |
| montmorillonite | |
| −60 mesh | 23–32 |
| montmorillonite | |
| −325 mesh | 21–28 |

[2] Determined using Speedy Moisture Tester Type D.1

For comparison, a run was also made with dry $CaSO_4.2H_2O$ fines, −60 mesh, at an atomization pressure of 2 bars and using a nozzle orifice of 1.2 millimeters.

The experimental results are tabulated in Table II, below.

TABLE II

| Fines | Run Time, min.:sec. | Charge Plaster, lbs. | Charge Fines, lbs. (wt. % H$_2$O) | Charge Plaster, wt. % | Charge Dry Fines, wt. % | Approximate Size Distribution, mesh % +20 | Approximate Size Distribution, mesh % 20/60 | Approximate Size Distribution, mesh % −60 | Bulk Density, lbs./ft.$^3$ | Surface Hardness, % attrition |
|---|---|---|---|---|---|---|---|---|---|---|
| CaSO$_4$ . 2H$_2$O −60 mesh | 1:00 | 25 | 36.0 (30) | 50 | 50 | 45.7 | 28.6 | 25.7 | 50 | 40 |
|  | 2:24 | 35 | 20.0 (30) | 70 | 30 | 64.2 | 26.1 | 9.7 | 50 | 35 |
|  | 4:00 | 40 | 11.0 (19) | 80 | 20 | 79.7 | 17.1 | 3.2 | 49 | 12 |
|  | 2:48 | 40 | 13.3 (25) | 80 | 20 | 62.8 | 27.4 | 9.8 | 51 | 38 |
|  | 6:00 | 42.5 | 9.3 (19) | 85 | 15 | 69.0 | 22.3 | 8.7 | 54 | 11 |
|  | 5:30 | 42.5 | 9.3 (19) | 85 | 15 | 60.8 | 24.7 | 14.5 | 53 | 14.6 |
|  | 3:24 | 45 | 6.75 (25) | 90 | 10 | 72.6 | 21.4 | 5.9 | 52 | 14 |
|  | 5:30 | 45 | 6.2 (19) | 90 | 10 | 68.5 | 21.9 | 9.6 | 53 | 14 |
|  | 4:45 | 42.5 | 7.5 (0) | 85 | 15 | 56.0 | 32.9 | 11.1 | 50 | 16.8 |
| montmorillonite −60 mesh | 4:24 | 25 | 37.9 (50) | 50 | 50 | 40.2 | 36.4 | 23.4 | 44 | 38 |
|  | 5:00 | 35 | 22.5 (33) | 70 | 30 | 61.0 | 28.1 | 11.1 | 43 | 36 |
|  | 5:00 | 40 | 15.5 (33) | 80 | 20 | 67.1 | 24.1 | 8.8 | 45 | 24 |
|  | 5:00 | 45 | 7.5 (33) | 90 | 10 | 66.8 | 24.7 | 8.5 | 49 | 17 |
| montmorillonite −325 mesh | 5:00 | 40 | 15.0 (34) | 80 | 20 | 66.2 | 23.1 | 10.7 | 44 | 36 |
|  | 5:00 | 45 | 7.6 (34) | 90 | 10 | 74.8 | 20.1 | 5.1 | 49 | 8 |
|  | 5:12 | 47.5 | 3.8 (34) | 95 | 5 | 74.2 | 19.7 | 6.1 | 52 | 12 |

EXAMPLE 3

The same granulator as in Example 1 was used to granulate charges of the same gypsum plaster as used in Example 1. The charges were fluidized with air at a temperature of about 115° F. (45° C.).

The binder in each instance was water, sprayed at different rates through a spray nozzle having an interchangeable orifice. The produced agglomerates were then recovered from the granulator, dried, and classified according to size. It was observed that in each instance the agglomerates retained on a 20-mesh screen were primarily gypsum macrogranules comprising a plurality of relatively smaller gypsum granules surface-bonded to one another.

The processing parameters for each charge and the obtained experimental results are set forth in Table III, below.

TABLE III

| Run | Charge Size, lbs. | Run Time, min.: sec. | Atom'n Press., bars | Nozzle Orifice, microns | Water Sprayed, ml. | Water Add-On, wt. % | Approximate Output Size Distribution, mesh % +20 | Approximate Output Size Distribution, mesh % 20/60 | Approximate Output Size Distribution, mesh % −60 | Bulk Density, lbs./ft.$^3$ | Surface Hardness, % attrition | +60 mesh Dihydrate Yield, lbs. |
|---|---|---|---|---|---|---|---|---|---|---|---|---|
| AD | 50 | 6:00 | 3 | 1.8 | 5100 | 17 | 36.6 | 34.3 | 29.0 | 52 | 10 | 56.75 |
| AE | 50 | 6:00 | 3 | 1.8 | 5350 | 18.5 | 50.4 | 30.0 | 20.0 | 53 | 8 | 55.00 |
| AF | 50 | 5:00 | 3 | 1.8 | 4750 | 18.5 | 46.2 | 28.0 | 25.7 | 53 | 8 | 56.25 |
| AG | 50 | 4:00 | 3 | 1.8 | 4500 | 18.5 | 42.0 | 31.1 | 26.6 | 53 | 9 | 56.25 |
| AH | 50 | 3:30 | 3 | 1.8 | 4300 | 19 | 41.9 | 32.1 | 25.9 | 53 | 7 | 53.00 |
| AI | 50 | 5:00 | 3 | 1.8 | 4000 | 17 | 25.6 | 35.3 | 39.1 | 53 | 16 | 53.75 |
| AJ | 50 | 5:00 | 3 | 1.8 | 4200 | 17 | 25.5 | 36.6 | 38.4 | 52 | 18 | 52.75 |
| AK | 50 | 5:00 | 3 | 1.8 | 4700 | 19 | 38.0 | 35.1 | 26.8 | 52 | 16 | 55.00 |
| AL | 50 | 5:00 | 3 | 1.8 | 4750 | 21 | 50.0 | 27.2 | 22.7 | 52 | 12 | 56.00 |
| AM | 50 | 4:17 | 3 | 1.8 | 4400 | 19 | 44.7 | 29.5 | 25.8 | 52 | 8 | 54.25 |
| AN | 50 | 10:00 | 3 | 1.2 | 5800 | 19 | 16.9 | 33.5 | 49.5 | N.D.[3] | N.D. | 54.50 |
| AO | 50 | 9:00 | 3 | 1.2 | 4500 | 15 | 18.4 | 34.2 | 47.2 | N.D. | N.D. | 54.35 |
| AP | 50 | 9:00 | 3 | 1.2 | 5370 | 18 | 24.3 | 37.6 | 39.3 | N.D. | N.D. | 52.50 |
| AQ | 50 | 9:00 | 3 | 1.2 | 6000 | 20 | 35.2 | 34.1 | 30.7 | N.D. | N.D. | 54.60 |
| AR | 50 | 9:00 | 3 | 1.2 | 6700 | 21 | 41.6 | 34.5 | 23.8 | N.D. | N.D. | 56.50 |
| AS | 50 | 9:00 | 3 | 1.2 | 7120 | 23 | 55.7 | 30.0 | 14.4 | N.D. | N.D. | 54.35 |
| AT | 50 | 9:00 | 1 | 1.2 | 5200 | 17 | 69.6 | 16.4 | 14.0 | N.D. | N.D. | 52.3 |
| AU | 50 | 9:00 | 2 | 1.2 | 5250 | 18 | 70.7 | 21.0 | 8.3 | N.D. | N.D. | 51.3 |
| AV | 50 | 9:00 | 4 | 1.2 | 5350 | 18.5 | 17.6 | 33.5 | 48.9 | N.D. | N.D. | 52.25 |
| AW | 50 | 9:00 | 5 | 1.2 | 5400 | 16 | 17.7 | 28.2 | 54.1 | N.D. | N.D. | 55.00 |
| AX | 50 | 9:00 | 5 | 1.2 | 6100 | 19 | 23.3 | 34.3 | 42.4 | N.D. | N.D. | 59.00 |
| AY | 50 | 9:00 | 5-4 | 1.2 | 6800 | 21 | 19.5 | 31.2 | 49.3 | N.D. | N.D. | 53.75 |
| AZ | 50 | 9:00 | 5 | 1.2 | 7450 | 23 | 34.1 | 39.8 | 26.2 | N.D. | N.D. | 57.25 |
| BA | 50 | 9:00 | 5 | 1.2 | 6800 | 21 | 27.0 | 39.6 | 33.4 | N.D. | N.D. | 58.35 |
| BB | 50 | 9:00 | 5 | 1.2 | 6800 | 21 | 32.0 | 26.5 | 17.9 | N.D. | N.D. | 57.55 |
| BC | 50 | 9:00 | 5 | 1.2 | 6800 | 21 | 39.6 | 33.0 | 27.4 | N.D. | N.D. | 56.85 |
| BD | 40 | 3:00 | 5 | 1.8 | 3700 | 18 | 50.8 | 24.9 | 24.3 | N.D. | N.D. | 43.25 |
| BE | 50 | 8:30 | 5 | 1.2 | 7200 | 21 | 32.7 | 36.7 | 30.4 | 51 | 9 | 55.75 |
| BF | 50 | 8:30 | 5 | 1.2 | 7200 | 23 | 43.4 | 33.5 | 23.1 | 52 | 18 | 55.25 |
| BG | 50 | 8:10 | 5 | 1.2 | 7200 | 19 | 38.3 | 31.7 | 30.0 | 52 | 10 | 57.50 |
| BH | 50 | 9:00 | 2 | 1.2 | 5300 | 17 | 35.0 | 37.7 | 27.2 | N.D. | N.D. | 55.00 |
| BI | 50[4] | 8:00 | 3 | 1.8 | 7000 | 19 | 46.1 | 36.2 | 17.7 | 55 | 17 | 58.00 |
| BJ | 50[4] | 4:30 | 3 | 1.8 | 5800 | 19 | 77.3 | 16.8 | 5.9 | 55 | 8 | 55.00 |
| BK | 50 | 4:45 | 3 | 1.8 | 5500 | 20 | 57.5 | 31.5 | 11.0 | 54 | 11 | 50.00 |
| BL | 50 | 2:15 | 3 | 1.8 | 4700 | 19 | 53.9 | 30.0 | 15.9 | 53 | 17 | 56.50 |
| BM | 50 | 7:00 | 3 | 1.2 | 6000 | 19 | 55.8 | 30.9 | 13.3 | 52 | 12 | 56.50 |
| BN | 50[4] | 7:00 | 3 | 1.8 | 8300 | 18 | 38.8 | 39.2 | 21.9 | 53 | 13 | 58.00 |
| BO | 50 | 5:00 | 5 | 1.8 | 5800 | 20 | 51.5 | 36.0 | 12.4 | 52 | 17 | 56.25 |

TABLE III-continued

| Run | Charge Size, lbs. | Run Time, min.: sec. | Atom'n Press., bars | Nozzle Orifice, microns | Water Sprayed, ml. | Water Add-On, wt. % | Approximate Output Size Distribution, mesh % +20 | % 20/60 | % −60 | Bulk Density, lbs./ft.³ | Surface Hardness, % attrition | +60 mesh Dihydrate Yield, lbs. |
|---|---|---|---|---|---|---|---|---|---|---|---|---|
| BP | 50 | 3:42 | 3 | 1.8 | 5320 | 21 | 65.3 | 26.5 | 8.2 | 53 | 10 | 54.75 |

³Not Determined
⁴aqueous 1% KCl spray; provides about 0.5 lbs. KCl

EXAMPLE 4

The granulated products produced in certain runs of Example 3 and retained on a 20-mesh screen (and comprising primarily gypsum macrogranules) were subsequently crushed using a roll-type crusher. The obtained crushed product in each case was classified according to particle size. The experimental results are reported in Table IV, below.

TABLE IV

| Run | Total amount of +20 particles lbs. | Approximate Size Distribution After Crushing, mesh % +20 | % 20/60 | % −60 | Percent Yield of 20/60 Granules Based On Feed | Output |
|---|---|---|---|---|---|---|
| AO | 9.5 | 5.0 | 77.0 | 18.0 | 51.6 | 47.4 |
| AQ | 18.8 | 6.6 | 72.0 | 21.3 | 68.1 | 62.4 |
| AR | 21.5 | 0 | 52.3 | 47.7 | 62.0 | 54.9 |
| AS | 23.5 | 3.1 | 71.3 | 25.5 | 66.2 | 60.8 |
| AV | 34.5 | 3.6 | 72.5 | 23.9 | 71.6 | 69.8 |

From the foregoing data it can be readily seen that the yield of absorbent granules in the desired 20/60-mesh size range can be maximized by subjecting the produced +20 granules, including the macrogranules, to a secondary size reduction by crushing. Also, in the foregoing runs the major portion of the granules constituting the macrogranules retained on the 20-mesh screen is in the 20/60 mesh size range.

EXAMPLE 5

The liquid holding capacity, and the oil and water absorption characteristics of 20/60 mesh gypsum granules produced by different manufacturing processes were determined using the techniques set forth hereinabove. The results are compiled in Table V, below.

TABLE V

| Manufacturing Process | Bulk Density, lbs./ft.³ | L.H.C., % | Oil ABsorption, ml./gm. | Water Absorption, ml./gm. |
|---|---|---|---|---|
| fluidized bed | ≈48 | 11.5 | .70 | .70 |
| fluidized bed + crushing⁵ | ≈48 | 13.6 | .70 | .96 |
| agricultural gypsum⁶ | 67.3 | 3.9 | .54 | .46 |

⁵+20 mesh granules crushed to 20/60 mesh particle size
⁶naturally-occurring gypsum crushed to 20/60 mesh particle size

We claim:
1. A gypsum-containing macrogranule which comprises an agglomerate of a plurality of relatively smaller, gypsum-containing granules that are surface-bonded to one another in a discrete cluster having a bulk density that is at least about 5 percent less than said gypsum-containing granules and an average diameter that is at least about twice the average diameter of a majority of said gypsum-containing granules.

2. The gypsum-containing macrogranule in accordance with claim 1 wherein said relatively smaller, gypsum-containing granules have a dry bulk density of less than about 55 pounds per cubic foot, a surface hardness of less than about 40 percent attrition, and a liquid holding capacity of at least about 10 percent by weight.

3. The gypsum-containing macrogranule in accordance with claim 1 having a size greater than about 20 mesh and having a major portion of the macrogranule constituted by granules having a size of about 20/60 mesh.

4. A low density gypsum-containing granule having an inner core portion comprising calcium sulfate dihydrate and hemihydrate and an outer shell portion consisting essentially of calcium sulfate dihydrate.

5. The low density gypsum-containing granule of claim 5 wherein the concentration of calcium sulfate dihydrate in the inner core portion increases with increasing radial distance from the center of the inner core portion.

* * * * *

UNITED STATES PATENT AND TRADEMARK OFFICE
CERTIFICATE OF CORRECTION

PATENT NO. : 4,183,763

DATED : January 15, 1980

INVENTOR(S) : Barry A. Omilinsky and Fredrick E. Wolatz

It is certified that error appears in the above-identified patent and that said Letters Patent are hereby corrected as shown below:

Col. 2, line 10, "6 to 8" should be -- 6 or 8 --.

Col. 2, line 54, "$CaSO_4.2H_2O$" should be -- $CaSO_4 \cdot 2H_2O$ --.

Col. 3, line 7, "$CaSO_4.\frac{1}{2}H_2O$" should be -- $CaSO_4 \cdot \frac{1}{2}H_2O$ --.

Col. 3, line 12, "$CaSO_4.2H_2O$" should be -- $CaSO_4 \cdot 2H_2O$ --.

Col. 10, line 17, "entitles" should be -- entities --.

Col. 13, line 52, "a a pair" should be -- a pair --.

Col. 14, line 57, "$CaSO_4.2H_2O$" should be -- $CaSO_4 \cdot 2H_2O$ --.

Col. 14, line 65, "$SO_4.2H_2O$" should be -- $SO_4 \cdot 2H_2O$ --.

Table II, col. 1, line 2, "$CaSO_4.2H_2O$" should be -- $CaSO_4 \cdot 2H_2O$ --.

Table II, col. 4, line 3, "(wt. % $H_2O$" should be -- (wt. % $H_2O$) --.

Table V, col. 4, line 2, "ABsorption," should be -- Absorption, --.

UNITED STATES PATENT AND TRADEMARK OFFICE
CERTIFICATE OF CORRECTION

PATENT NO. : 4,183,763

DATED : January 15, 1980

INVENTOR(S) : Barry A. Omilinsky and Fredrick E. Wolatz

It is certified that error appears in the above-identified patent and that said Letters Patent are hereby corrected as shown below:

Table V, col. 2, line 4, "≋48" should be -- ∿48 --.

Table V, col. 2, line 5, "≋48" should be -- ∿48 --

Col. 18, line 47, "claim 5" should be -- claim 4 --.

Signed and Sealed this

Thirteenth Day of May 1980

[SEAL]

Attest:

SIDNEY A. DIAMOND

Attesting Officer     Commissioner of Patents and Trademarks